(12) United States Patent
Wang et al.

(10) Patent No.: US 11,865,503 B2
(45) Date of Patent: Jan. 9, 2024

(54) MULTIPURPOSE SOLUTION MIXER AND USE METHOD THEREOF

(71) Applicant: Shanghai University of Traditional ChineseMedicine, Shanghai (CN)

(72) Inventors: Jianying Wang, Shanghai (CN); Lei Zhang, Shanghai (CN); Xiaojuan Hu, Shanghai (CN)

(73) Assignee: SHANGHAI UNIVERSITY OF TRADITIONAL CHINESE MEDICINE, Shanghai (CN)

( * ) Notice: Subject to any disclaimer, the term of this patent is extended or adjusted under 35 U.S.C. 154(b) by 926 days.

(21) Appl. No.: 16/831,633

(22) Filed: Mar. 26, 2020

(65) Prior Publication Data

US 2020/0316541 A1 Oct. 8, 2020

(30) Foreign Application Priority Data

Apr. 4, 2019 (CN) .......................... 201910272948.5

(51) Int. Cl.
*B01F 33/84* (2022.01)
*A61M 11/04* (2006.01)
(Continued)

(52) U.S. Cl.
CPC ......... *B01F 33/846* (2022.01); *A61M 11/041* (2013.01); *A61M 21/02* (2013.01);
(Continued)

(58) Field of Classification Search
CPC ............. B01F 35/2209; B01F 2101/22; B01F 33/844; B01F 33/8442; B01F 33/846
(Continued)

(56) References Cited

U.S. PATENT DOCUMENTS

2008/0029541 A1 * 2/2008 Wallace ............... B67D 1/0021
222/207
2008/0047972 A1 * 2/2008 Bartholomew ....... B01F 33/844
222/144.5

(Continued)

FOREIGN PATENT DOCUMENTS

WO WO-2008046518 A1 * 4/2008 ............. A45D 34/00

*Primary Examiner* — Marc C Howell
(74) *Attorney, Agent, or Firm* — Mark C. Johnson; Johnson Dalal

(57) ABSTRACT

A multipurpose solution mixer and a use method thereof are provided. The multipurpose solution mixer includes a main control unit, a solution storage unit and a solution blending unit installed in a case; an operation display unit and a liquid outlet provided on the case; and an atomization humidifying unit connected with the liquid outlet, wherein the main control unit is electrically connected with other units; the operation display unit is a display screen with touch operation functions; the solution storage unit includes sealed bottles and infusion tubes; the solution blending unit includes micropumps infusion tubes and a blending chamber, the blending chamber is connected with the atomization humidifying unit via respective infusion tubes, and the operation display unit sends instructions to the main control unit to control the micropumps to extract solutions from the sealed bottles into the blending chamber, and output a mixed solution via the liquid outlet.

18 Claims, 3 Drawing Sheets

(51) Int. Cl.
*A61M 21/02* (2006.01)
*F24F 6/12* (2006.01)
*B01F 23/40* (2022.01)
*B01F 23/21* (2022.01)
*B01F 33/82* (2022.01)
*B01F 35/83* (2022.01)
*B01F 35/22* (2022.01)
*A61M 21/00* (2006.01)
*B01F 101/22* (2022.01)
*B01F 101/00* (2022.01)

(52) U.S. Cl.
CPC ............ *B01F 23/211* (2022.01); *B01F 23/49* (2022.01); *B01F 33/82* (2022.01); *B01F 35/2209* (2022.01); *B01F 35/83* (2022.01); *F24F 6/12* (2013.01); *A61M 2021/0016* (2013.01); *A61M 2205/3379* (2013.01); *A61M 2205/3584* (2013.01); *A61M 2205/505* (2013.01); *B01F 2101/22* (2022.01); *B01F 2101/2202* (2022.01)

(58) Field of Classification Search
USPC ........................................ 222/145.6
See application file for complete search history.

(56) References Cited

U.S. PATENT DOCUMENTS

| | | | |
|---|---|---|---|
| 2008/0170462 A1* | 7/2008 | Ueda .................. | B01F 25/83 366/101 |
| 2009/0310856 A1* | 12/2009 | Korenkiewicz .......... | C09D 7/41 382/165 |
| 2014/0082854 A1* | 3/2014 | Landa .................. | A45D 19/02 356/402 |
| 2015/0314246 A1* | 11/2015 | Lehtonen ............ | B01F 35/2134 700/265 |
| 2018/0125206 A1* | 5/2018 | Shami ................ | B05C 11/1036 |
| 2019/0030502 A1* | 1/2019 | Ellsworth ............ | C09D 167/08 |

* cited by examiner

MULTIPURPOSE SOLUTION MIXER AND USE METHOD THEREOF

CROSS REFERENCE TO RELATED APPLICATIONS

The present disclosure claims priority to Chinese Patent Application No. 201910272948.5, filed with the Chinese Patent Office on Apr. 4, 2019 and entitled "Multipurpose Solution Mixer and Use Method Thereof", the entire contents of which are incorporated herein by reference.

TECHNICAL FIELD

The present disclosure relates to the technical field of solution preparation, and in particular to a multipurpose solution mixer (mixing device) and a use method thereof.

BACKGROUND ART

At present, in the prior art, how to obtain a device which is developed with an authoritative medical background and can quickly prepare essential oil solution and give guidance on aromatherapy health care with high cost performance is a problem to be solved urgently by those skilled in the art.

SUMMARY

Objects of the present disclosure includes providing a multipurpose solution mixer and a use method thereof.

Embodiments of the present disclosure provide a multipurpose solution mixer, including a main control unit, an operation display unit, a solution storage unit, a solution blending unit, an atomization humidifying unit and a liquid outlet, wherein the main control unit, the solution storage unit and the solution blending unit are installed in a case, the operation display unit and the liquid outlet are mounted to a body of the case; the main control unit is electrically connected with the operation display unit, the solution storage unit, the solution blending unit and the atomization humidifying unit; the operation display unit is a display screen with touch operation functions; the solution storage unit includes multiple sealed bottles and infusion tubes; the solution blending unit includes multiple micropumps, infusion tubes and a blending chamber, wherein two ends of each micropump are respectively connected with different sealed bottles or with the blending chamber via respective infusion tubes, the blending chamber is connected with the atomization humidifying unit via the corresponding infusion tube, and the atomization humidifying unit is connected with the liquid outlet; and the operation display unit is configured to send instructions to the main control unit to control the micropumps to extract solutions from the sealed bottles into the blending chamber to carry out mixing and output a mixed solution via the liquid outlet.

Embodiments of the present disclosure further provide a use method of the multipurpose solution mixer, in which the above described multipurpose solution mixer is used, and the following steps are executed:

Step 1: opening the case of the solution mixer, placing sealed bottles containing different solutions into respective slots, inserting infusion tubes until reaching the bottoms of the respective sealed bottles, and closing the case;

Step 2: inputting on a display screen a name of the solution in each sealed bottle placed in the slot having a corresponding sequential number;

Step 3: inputting at least one key word on the display screen by a touch operation, making a single-chip microcomputer in the main control unit retrieve a solution blending program from the storage device and displaying a preparation proportion on the screen for the user to confirm;

Step 4: the single-chip microcomputer controlling the micropumps by a motor control board to extract solutions from different sealed bottles, such that the extracted solutions form a mixed solution after entering the blending chamber, and outputting the mixed solution to a liquid outlet; and Step 5: placing a corresponding container on a liquid receiving tray to receive the mixed liquid output from the liquid outlet, so as to complete a solution mixing.

DETAILED DESCRIPTION OF DRAWINGS

In order to more clearly describe technical solutions of the embodiments of the present disclosure, brief descriptions on the drawings required to be used in the embodiments are made below. It is to be understood that the drawings are illustrative of some embodiments of the present disclosure and thus should not be construed as limitations on the scope, and for those of ordinary skills in the art, other drawings can also be obtained based on these drawings without inventive effort.

Figure 1:
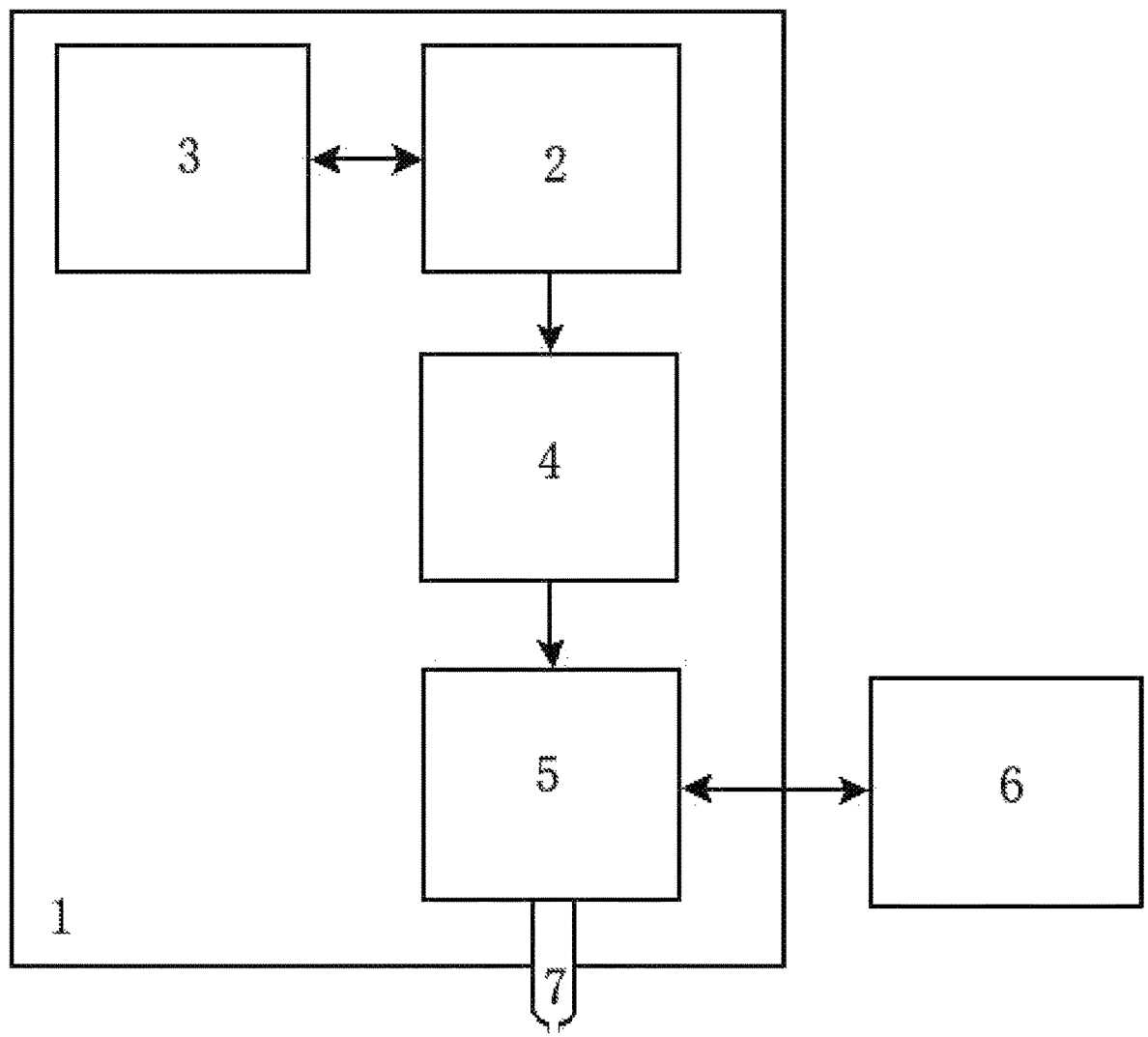
FIG. 1 is a schematic diagram showing an overall structure of a case according to embodiments of the present disclosure.
Figure 2:
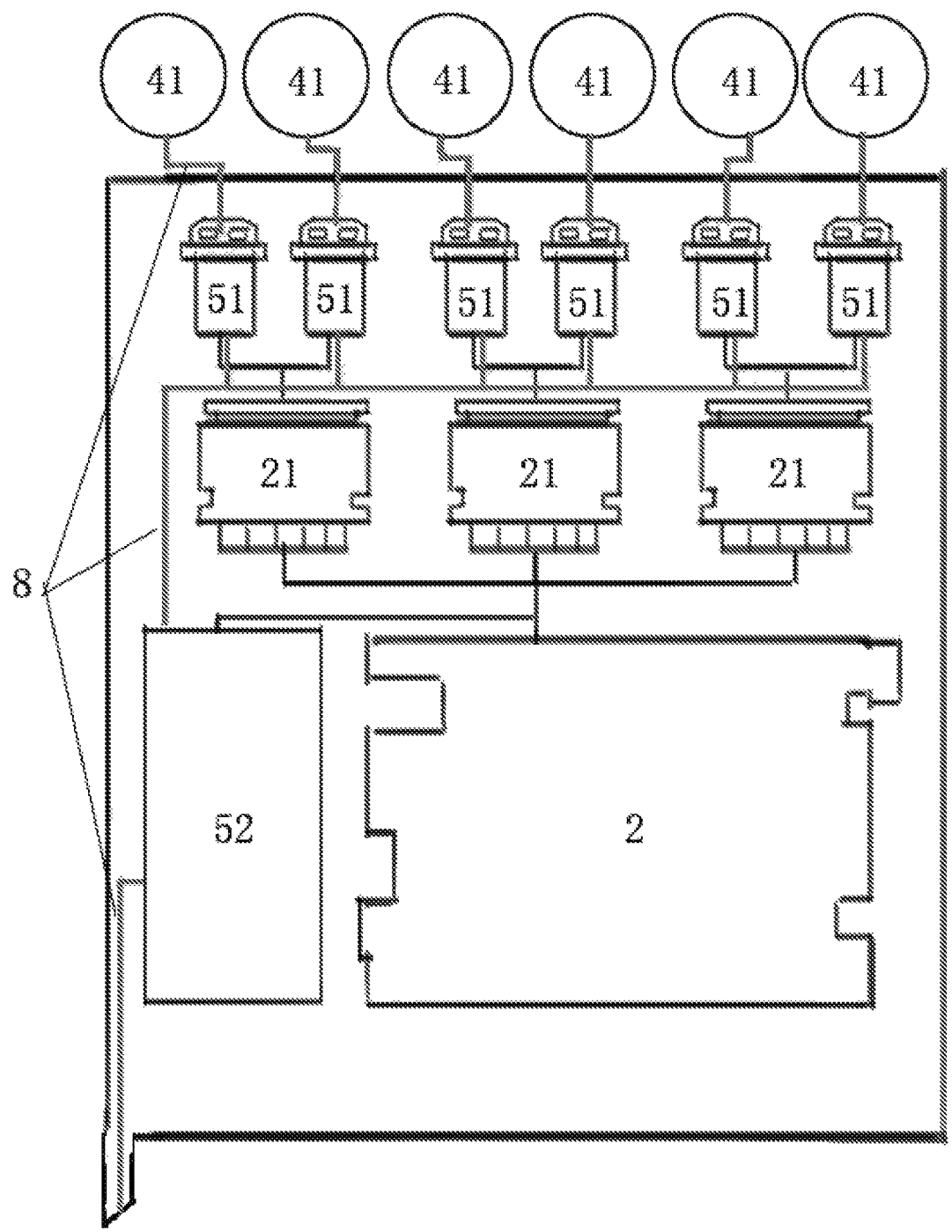
FIG. 2 is a schematic diagram showing an internal structure of the case according to embodiments of the present disclosure.
Figure 3:
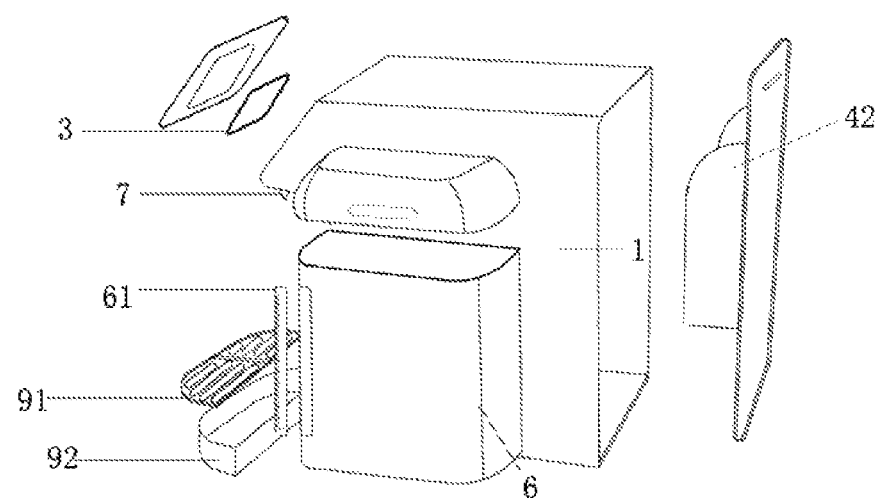
FIG. 3 is a schematic diagram showing appearance of a solution mixer according to embodiments of the present disclosure.

Reference signs: 1—case; 2—main control unit; 21—motor control board; 3—operation display unit; 4—solution storage unit; 41—sealed bottle; 42—slot; 5—solution blending unit; 51—micropump; 52—blending chamber; 6—atomization humidifying unit; 61—dial gauge; 7—liquid outlet; 8—infusion tube; 91—liquid receiving tray; 92—liquid collecting tray.

DETAILED DESCRIPTION OF EMBODIMENTS

In order to make clearer the objects, technical solutions and advantages of the embodiments of the present disclosure, the technical solutions of the present disclosure are to be clearly and entirely described below with reference to drawings of the embodiments of the present disclosure, it is apparent that the embodiments to be described are some, rather than all of the embodiments of the present disclosure. The components of the embodiments of the present disclosure as described and illustrated in the drawings herein may usually be arranged and designed in different configurations.

Therefore, the detailed description on the embodiments of the present disclosure provided with the drawings is not intended to limit the scope of protection of the present disclosure, but is merely illustrative of selected embodiments of the present disclosure. Based on embodiments of the present disclosure, all other embodiments made without inventive efforts by a skilled person in the art shall fall within the protection scope of the present disclosure.

It is to be noted that the features in the embodiments of the present disclosure may be combined with each other without conflict.

Life cultivation, health preservation, and "preventive treatment of disease" are daily life topics commonly concerned by the public, while aromatherapy plays one of the above. Aromatherapy is a type of auxiliary medical treatment that can prevent physical and mental diseases and provide health care effect by taking the essential oil extracted from fragrant plants as the medium and make it enter the body through respiratory system or skin system by gently smelling, fragrance expanding, massaging, bathing, and so on. An effective aromatherapy can create an atmosphere and improve one's creativity and work efficiency. Plant essential oil is the key substance of aromatherapy, different essential oils and mixing program can stimulate cerebral cortex by senses of vision and smell, so as to enlighten thinking, relieve psychological and spiritual pressures to make body and mind comfortable.

At present, people can obtain essential oil health cares in two manners: offline training or health care association, online network search or circle of referring to social media. The former is expensive and only a few organizations possess relevant qualifications, while the latter is easily available but has lower reliability and authenticity. Because of limitations on the use of pure essential oil, the essential oil used in aromatherapy is usually compound essential oil, that is to say, at least 2-5 single essential oils should be mixed up in a reasonable proportion with a large amount of base oil before use. Moreover, due to the fact that the essential oil is expensive, the unit taken during the mixing is mostly drop, in the case that the bottle cap is loose or too tight, it is difficult to control the quantity, therefore, for most people who don't have a medical background, how to perform the mixing will be a difficult knowledge. If there is a device which is developed with an authoritative medical background and can quickly prepare essential oil solution and give guidance on aromatherapy health care with high cost performance, most of the above problems will be solved. The device should be researched and developed urgently, and has a great market and application potential.

The multipurpose solution mixer and the use method thereof provided in the present disclosure can further facilitate a user to perform the operation of mixing solutions, thereby effectively alleviating the above problems present in the prior art.

The multipurpose solution mixer and the use method thereof provided in the present disclosure are to be described below in detail with reference to the drawings and detailed embodiments.

As shown in FIG. 1, embodiments of the present disclosure provide a multipurpose solution mixer, including a main control unit 2, an operation display unit 3, a solution storage unit 4, a solution blending unit 5, an atomization humidifying unit 6 and a liquid outlet 7, wherein the main control unit 2, the solution storage unit 4 and the solution blending unit 5 are installed in a case 1, the operation display unit 3 and the liquid outlet 7 are provided on the case 1; the main control unit 2 is electrically connected with other units; the operation display unit 3 is a display screen with touch operation functions; the solution storage unit 4 includes multiple sealed bottles 41 and infusion tubes 8; the solution blending unit 5 includes multiple micropumps 51, infusion tubes 8 and a blending chamber 52, wherein two ends of each micropump 51 are respectively connected with different sealed bottles 41 or with the blending chamber 52 via respective infusion tubes 8, the blending chamber 52 is connected with the atomization humidifying unit 6 via the corresponding infusion tube 8, and the atomization humidifying unit 6 is connected with the liquid outlet 7; and the operation display unit 3 is configured to send instructions to the main control unit 2 to control the micropumps 51 to extract solutions from the sealed bottles 41 into the blending chamber 52 to carry out mixing and output a mixed solution via the liquid outlet 7.

Optionally, the main control unit 2 includes a single-chip microcomputer, a motor control board 21, a storage device, a communication device, and a power supply device, wherein the single-chip microcomputer is configured to control each unit and each device, the storage device is configured to store solution blending program, the communication device is configured to receive remote instructions after being connected to a network, so as to operate the solution mixer or to download new solution blending program from the network and store them in the storage device, the motor control board 21 is configured to control running of the micropumps 51, and the power supply device is configured to supply power to each unit.

Optionally, intelligent learning software is loaded in the single-chip microcomputer, wherein the intelligent learning software can customize and recommend solution blending program in a personalized manner according to using habits of the user.

Optionally, the atomization humidifying unit 6 is arranged outside the case 1 and located at one side of the case, wherein the atomization humidifying unit includes a switch, an infusion tube, a water storage tank and an atomizer, wherein a shell of the atomization humidifying unit 6 is provided with a dial gauge 61 configured to indicate the volume of the water in the water storage tank, the blending chamber 52 and the water storage tank are both connected to the atomizer through the infusion tubes 8, and the mixed solution is first atomized and humidified by the atomizer and then output from the liquid outlet.

Optionally, the solution storage unit 4 is provided with multiple slots 42, wherein each slot 42 has a different sequential number and is mounted on an inner side plate of the case, each sealed bottle 41 is placed in a separate slot, and various solutions are stored in the sealed bottles 41, each sealed bottle 41 is provided with one seal cover, with the seal cover screw-capped thereon, wherein an end of the respective infusion tube 8 penetrates the seal cover and reaches the bottom of the sealed bottle 41.

Optionally, each infusion tube 8 is a replaceable capillary tube having an orifice diameter of 0.5-3 mm.

Optionally, a liquid collecting tray 92 and a liquid receiving tray 91 which are connected with the case are provided below the liquid outlet 7, wherein the liquid receiving tray 91 is provided with multiple holes and is mounted on the liquid collecting tray 92, and leaked solution first drips on the liquid receiving tray 91 and then flows onto the liquid collecting tray 92 via the holes.

Optionally, the solution includes, but is not limited to, any one of essential oil stocks, solvents and beverages.

Embodiments of the present disclosure further provide a use method of the multipurpose solution mixer, in which the above described multipurpose solution mixer is used, and the following steps are executed:

Step 1: opening the case of the solution mixer, placing sealed bottles containing different solutions into respective slots, inserting infusion tubes which reach the bottoms of the respective sealed bottles, and closing the case;

Step 2: inputting on a display screen a name of the solution in each sealed bottle placed in the slot having a corresponding sequential number;

Step 3: inputting at least one key word on the display screen by a touch operation, making the single-chip microcomputer in the main control unit retrieve a solution blending program from the storage device and displaying a preparation proportion on the screen for the user to confirm;

Step 4: the single-chip microcomputer controlling the micropumps by a motor control board to extract solutions from different sealed bottles, such that the extracted solutions form a mixed solution after entering the blending chamber, and outputting the mixed solution to a liquid outlet; and Step 5: placing a corresponding container on a liquid receiving tray to receive the mixed liquid output from the liquid outlet, so as to complete a solution mixing.

Optionally, in Step 3, if the user is not satisfied with the solution blending program in the storage unit, the solution mixer can receive, after being connected to a network via the communication device, remote instructions to operate the solution mixer or download new solution blending program from the network and store them in the memory device, or the user may finely adjust the proportion manually until being satisfied, and then make reconfirmation.

Optionally, in Step 4, selection is performed on the display screen to input the mixed solution into the atomization humidifying unit, such that the mixed solution is atomized and humidified, and then output from the liquid outlet.

Optionally, the user may operate the solution mixer, by using the communication device to perform remote connection, instead of by operating on the display screen.

Optionally, the user can put different types of single essential oil and base oil purchased on the market into the sealed bottles in slots of the case of solution mixer, then input on the display screen the names of the essential oils placed in the sealed bottles in the slots having corresponding sequential numbers, so as to complete a preparation operation; when essential oil blending is needed, keywords about seasons, moods and symptoms such as: spring, refreshing, sleep, happiness and so on may be input on the display screen and the main control unit retrieves a solution blending program, wherein if the user is not satisfied with the solution blending program, he/she can update a formula from the network (Internet) or make fine adjustment on the formula, and makes a confirmation until satisfactory; and after blending the essential oils according to the formula, the solution (essence oil) mixer outputs the compound essential oil.

Optionally, the user can remotely control the solution mixer via a mobile phone APP by inputting keywords about seasons, moods and symptoms such as: spring, refreshing, sleep, and happiness and so on. After selecting a formula, the user may choose to turn on the atomization humidifying unit to make the solution (essence oil) mixer blend the essential oils according to the formula and then atomize and humidify the mixed solution, such that the room is humidified with fragrance.

Optionally, the user can adjust the contents of the solutions in the sealed bottles and the solution blending program to complete the mixture and preparation of solutions in various fields such as scientific research and beverage, so as to meet the needs of all aspects from preparing normal saline to blending cocktails.

Optionally, large cases and large sealed bottles may be used in the solution mixer, and the mixer may be placed in a public outdoor area, and users may make payments and selections remotely via a network, to get mixed solutions on site, thus the commercial needs can be met.

The beneficial effects brought by the multipurpose solution mixer and the use method thereof provided in the present disclosure includes, for example:

1) The flow (volume) of liquid in each micropump is controlled by a microcomputer chip to avoid the error and contamination caused by manually pouring solutions, so as to improve the preparation efficiency and facilitate daily operations.
2) Inaccurate flow caused by blocking of tubes or cross-contamination may be avoided by using replaceable capillary tubes to convey the solution.
3) The storage device may store various solution blending program, which can also be updated online via the communication device.
4) The single-chip microcomputer can perform intelligent learning according to a usage pattern of the user to provide personalized blending program.

What is described above is merely a selection of optional embodiments of the present disclosure and is not intended to limit the present disclosure, and any modification, equivalent substitution and improvement, made within the principle and essence of the present disclosure, shall all be covered by the scope of protection of the present disclosure.

What is claimed is:

1. A multipurpose solution mixer, comprising:
a main control unit, an operation display unit, a solution storage unit, a solution blending unit, an atomization humidifying unit and a liquid outlet, wherein the main control unit, the solution storage unit and the solution blending unit are installed in a case, and the operation display unit and the liquid outlet are mounted to a body of the case;
the main control unit is electrically connected with the operation display unit, the solution storage unit, the solution blending unit and the atomization humidifying unit;
the operation display unit is a display screen with touch operation functions;
the solution storage unit comprises at least two sealed bottles and infusion tubes;
the solution blending unit comprises at least two micropumps, infusion tubes and a blending chamber, wherein two ends of each micropump are respectively connected with different of the at least two sealed bottles or with the blending chamber via respective infusion tubes, the blending chamber is connected with the atomization humidifying unit via a corresponding infusion tube, and the atomization humidifying unit is connected with the liquid outlet; and
the operation display unit is configured to send instructions to the main control unit to control the at least two micropumps to extract solutions from the at least two sealed bottles into the blending chamber to carry out mixing, and output a mixed solution via the liquid outlet,
wherein the atomization humidifying unit is arranged outside the case and located at one side of the case,
the atomization humidifying unit comprises a switch, an infusion tube, a water storage tank and an atomizer, wherein a shell of the atomization humidifying unit is provided with a dial gauge configured to indicate a water volume in the water storage tank, and the blending chamber and the water storage tank are both connected to the atomizer, wherein the mixed solution is first atomized and humidified by the atomizer and then output from the liquid outlet.

2. The multipurpose solution mixer according to claim 1, wherein the main control unit comprises a single-chip microcomputer, a motor control board, a storage device, a communication device, and a power supply device, wherein the single-chip microcomputer is configured to control each of the main control unit, the operation display unit, the solution storage unit, the solution blending unit and the atomization humidifying unit and each of the storage device, the communication device and the power supply device, the storage device is configured to store a solution blending program, the communication device is configured to receive remote instructions after being connected to a network, so as to operate the solution mixer or to download a new solution blending program from the network and store the new solution blending program in the storage device, the motor control board is configured to control running of the at least two micropumps, and the power supply device is configured to supply power to each of the main control unit, the operation display unit, the solution storage unit, the solution blending unit and the atomization humidifying unit.

3. The multipurpose solution mixer according to claim 2, wherein an intelligent learning software is loaded in the single-chip microcomputer, and the intelligent learning software is configured to customize and recommend a solution blending program in a personalized manner according to using habits of a user.

4. The multipurpose solution mixer according to claim 1, wherein the solution storage unit is provided with a plurality of slots, wherein each slot has a different sequential number and is mounted on an inner side plate of the case, the at least two sealed bottles are placed in respective slots, and configured to store various solutions respectively, and each of the least two sealed bottles is provided with one seal cover, with the seal cover screw-capped thereon, wherein an end of a corresponding infusion tube penetrates the seal cover and reaches a bottom of the at least two sealed bottles.

5. The multipurpose solution mixer according to claim 1, wherein each infusion tube is a replaceable capillary tube having an orifice diameter of 0.5-3 mm.

6. The multipurpose solution mixer according to claim 1, wherein a liquid collecting tray and a liquid receiving tray which are connected with the case are provided below the liquid outlet, and the liquid receiving tray is provided with at least two holes and is mounted on the liquid collecting tray, wherein leaked solution is operably configured to first drip on the liquid receiving tray and then flows onto the liquid collecting tray via the at least two holes.

7. The multipurpose solution mixer according to claim 1, wherein the solution in each of the at least two sealed bottles is any one selected from the group consisting of essential oil stocks, solvents and beverages.

8. A use method of a multipurpose solution mixer comprising the following steps of:

Step 1: opening a case of the multiple purpose solution mixer, placing at least two sealed bottles containing different solutions into respective slots located thereon, inserting infusion tubes which reach bottoms of the respective of the least two sealed bottles, and closing the case;

Step 2: inputting on a display screen a name of the solution in each of the at least two sealed bottles placed in the slots having a corresponding sequential number;

Step 3: inputting at least one key word on the display screen by a touch operation, making a single-chip microcomputer in a main control unit to retrieve a solution blending program from a storage device and displaying a preparation proportion on the screen for the user to confirm;

Step 4: the single-chip microcomputer controlling at least two micropumps by a motor control board to extract solutions from different of the at least two sealed bottles such that the extracted solutions form a mixed solution after entering the blending chamber, and outputting the mixed solution to a liquid outlet; and Step 5: placing a container on a liquid receiving tray to receive the mixed liquid output from the liquid outlet, so as to complete a solution mixing wherein an atomization humidifying unit is arranged outside the case and located at one side of the case, the atomization humidifying unit comprises a switch, an infusion tube, a water storage tank and an atomizer, wherein a shell of the atomization humidifying unit is provided with a dial gauge configured to indicate a water volume in the water storage tank, and the blending chamber and the water storage tank are both connected to the atomizer, wherein the mixed solution is first atomized and humidified by the atomizer and then output from the liquid outlet.

9. The use method of multipurpose solution mixer according to claim 8, wherein the main control unit comprises the single-chip microcomputer, the motor control board, the storage device, a communication device, and a power supply device, wherein the single-chip microcomputer is configured to control each of the main control unit, the operation display unit, the solution storage unit, the solution blending unit and the atomization humidifying unit and each of the storage device, the communication device and the power supply device, the storage device is configured to store solution blending program, the communication device is configured to receive remote instructions after being connected to a network, so as to operate the solution mixer or to download new solution blending program from the network and store the new solution blending program in the storage device, the motor control board is configured to control running of the at least two micropumps, and the power supply device is configured to supply power to each of the main control unit, the operation display unit, the solution storage unit, the solution blending unit and the atomization humidifying unit.

10. The use method of multipurpose solution mixer according to claim 9, wherein an intelligent learning software is loaded in the single-chip microcomputer, and the intelligent learning software is used to customize and recommend solution blending program in a personalized manner according to using habits of a user.

11. The use method of multipurpose solution mixer according to claim 8, wherein the solution storage unit is provided with a plurality of slots, wherein each slot has a different sequential number and is mounted on an inner side plate of the case, the at least two sealed bottles are placed in respective slots, and configured to store various solutions respectively, and each of the at least two sealed bottles is provided with one seal cover, with the seal cover screw-capped thereon, wherein an end of a corresponding infusion tube penetrates the seal cover and reaches a bottom of the of the at least two sealed bottles.

12. The use method of multipurpose solution mixer according to claim 8, wherein each infusion tube is a replaceable capillary tube having an orifice diameter of 0.5-3 mm.

13. The use method of multipurpose solution mixer according to claim 8, wherein a liquid collecting tray and a liquid receiving tray which are connected with the case are provided below the liquid outlet, and the liquid receiving tray is provided with at least two holes and is mounted on the liquid collecting tray, wherein leaked solution first drips on the liquid receiving tray and then flows onto the liquid collecting tray via the holes.

14. The use method of multipurpose solution mixer according to claim 8, wherein the solution in each of the at least two sealed bottles is any one selected from the group consisting of essential oil stocks, solvents and beverages.

15. The use method of multipurpose solution mixer according to claim 8, wherein the user accesses to a network via the communication device to download a new solution blending program and store the new solution blending program in the memory device, or the user finely adjusts a proportion manually until being satisfied, then makes reconfirmation.

16. The use method of multipurpose solution mixer according to claim 8, wherein the user selects on the display screen to input the mixed solution into the atomization humidifying unit, such that the mixed solution is atomized and humidified, and then output from the liquid outlet.

17. The use method of multipurpose solution mixer according to claim 8, wherein the user operates the solution mixer, by using the communication device to perform remote connection, instead of by operating on the display screen.

18. The use method of multipurpose solution mixer according to claim 9, wherein the user operates the solution mixer, by using the communication device to perform remote connection, instead of by operating on the display screen.

\* \* \* \* \*